United States Patent [19]
Bartlett et al.

[11] Patent Number: 5,494,911
[45] Date of Patent: Feb. 27, 1996

[54] ISOXAZOLE-4-CARBOXAMIDES AND HYDROXYALKYLIDENECYANOACET-AMIDES, PHARMACEUTICALS CONTAINING THESE COMPOUNDS AND THEIR USE

[75] Inventors: Robert R. Bartlett, Darmstadt; Friedrich-Johannes Kämmerer, Hochheim am Main, both of Germany

[73] Assignee: Hoechst Aktiengesellschaft, Frankfurt am Main, Germany

[21] Appl. No.: 938,048

[22] PCT Filed: Oct. 24, 1990

[86] PCT No.: PCT/EP90/01800

§ 371 Date: Nov. 16, 1992

§ 102(e) Date: Nov. 16, 1992

[87] PCT Pub. No.: WO91/17748

PCT Pub. Date: Nov. 28, 1991

[30] Foreign Application Priority Data

May 26, 1990 [DE] Germany .......................... 40 17 043.8
May 26, 1990 [DE] Germany .......................... 40 17 020.9
May 18, 1990 [DE] Germany .......................... 40 16 178.1

[51] Int. Cl.$^6$ .................... A61K 31/41; C07D 261/06
[52] U.S. Cl. ............... 514/256; 514/226.8; 514/228.8; 514/275; 514/326; 514/340; 514/378; 514/619; 514/626; 544/322; 544/326; 544/328; 544/330; 544/331; 544/54; 544/55; 544/96; 546/206; 546/275; 548/248; 564/194; 564/195; 564/196; 564/197; 564/198; 564/163; 564/168
[58] Field of Search .................... 514/378, 340, 514/256, 275, 226.8, 228.8, 326, 378, 340, 619, 626; 548/248; 544/322, 326, 328, 330, 331, 54, 55, 96; 546/206, 275; 564/197, 198, 194, 195, 196, 163, 168

[56] References Cited

U.S. PATENT DOCUMENTS 4,061,767 12/1977 Ertel et al. .............................. 558/414
4,087,535 5/1978 Heubach ................................. 558/414
4,892,963 1/1990 Gallagher et al. ...................... 558/414

FOREIGN PATENT DOCUMENTS

| | | |
|---|---|---|
| 1102341 | 6/1981 | Canada . |
| 1129867 | 8/1982 | Canada . |
| 1275251 | 9/1986 | Canada . |
| 257882 | 3/1988 | European Pat. Off. . |
| 274443 | 7/1988 | European Pat. Off. . |
| 2557003 | 6/1977 | Germany . |
| 2555789 | 7/1977 | Germany . |
| 3405727A1 | 8/1985 | Germany .............................. 546/208 |
| 211139 | 4/1988 | New Zealand . |
| 221352 | 10/1989 | New Zealand . |

OTHER PUBLICATIONS

Chemotherapy of Cancer, Second Ed., Carter et al., John Wiley & Sons, pp. 364–365, 1981.

Robert R. Bartlett, "Immunopharmacological Profile of HWA 486, A Novel Isoxazol Derivative—II. In Vivo Immunomodulating Effects Differ From Those of Cyclophosphamide, Prednisolone, or Cyclosporin A," Int. J. Immunopharmac., vol. 8, No. 2, pp. 199–204, 1986.

R. R. Bartlett, et al., "Development of Autoimmunity in MRL/lpr Mice and the Effects of Drugs on This Murine Disease," Scand. J. Rheumatology 1988; Suppl. 75: 290–299.

Primary Examiner—Joseph K. McKane
Attorney, Agent, or Firm—Finnegan, Henderson, Farabow, Garrett & Dunner

[57] ABSTRACT

Isoxazole-4-carboxamide derivatives and hydroxyalkylidene-cyanoacetamide derivatives are suitable for the treatment of carcinoses. These compounds can be prepared by known processes. Some of the compounds are novel and are additionally suitable for the treatment of rheumatic disorders.

22 Claims, No Drawings

ISOXAZOLE-4-CARBOXAMIDES AND HYDROXYALKYLIDENECYANOACET-AMIDES, PHARMACEUTICALS CONTAINING THESE COMPOUNDS AND THEIR USE

A number of processes for the preparation of isoxazole-4-carboxamides have been described in the literature (DE 2,524,959; DE 2,655,009; DE 3,405,727).

It is known from European Patent Specification 13,376 that 5-methylisoxazole-4-carboxylic acid-(4-trifluoromethyl)anilide can be employed as an antirheumatic, antiinflammatory, antipyretic and analgesic owing to its pharmacological properties, and is used for the treatment of multiple sclerosis. Processes for the preparation of this compound are also described therein.

It has now been found that isoxazole-4-carboxamides of the formula I and hydroxyalkylidenecyanoacetamides of the formula Ia and their tautomeric form Ib have antitumor activity. Many of the known antitumor agents cause nausea, vomiting or diarrhea as adverse effects during treatment, which also make medical treatment in hospital necessary. In addition, these pharmaceuticals also modify the growth rate of other body cells, which then leads to symptoms such as, for example, hair loss or anemia. It was not possible to observe these symptoms in the treatment of humans and animals with the compounds of the formula I. In contrast to the cytotoxic anticancer agents known to date, these active compounds do not have the property of impairing the immune system (Bartlett, Int. J. Immunopharmac., 1986, 8: 199–204). Novel routes of tumor therapy are thus opened up as the body's defense system is not impaired, while tumor cells are prevented from growth. Surprisingly, a plurality of tumor cells are inhibited by these active compounds, while cells of the immune system, such as, for example, T lymphocytes are only inhibited at a concentration of up to 50 times higher.

The invention therefore relates to the use of at least one compound of the formula I, Ia and Ib

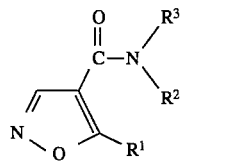

(I)

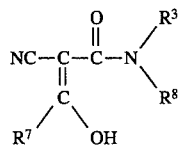

(Ia)

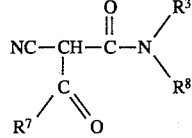

(Ib)

its possible stereoisomeric forms and/or if appropriate at least one of its physiologically tolerable salts, in which $R^1$ is
 a) hydrogen,
 b) alkyl having 1 to 6 carbon atoms,
 c) alkyl having 1 to 4 carbon atoms, mono- or polysubstituted by
  1) halogen, such as fluorine, chlorine, bromine or iodine,
 d) phenyl, $R^2$ is
 a) hydrogen,
 b) alkyl having 1 to 4 carbon atoms,
 c) phenyl-$(C_1-C_2)$-alkyl, in particular benzyl,
 d) alkenyl having 2 to 3 carbon atoms, $R^3$ is
 a) a mono-, di- or trinuclear, unsaturated heterocyclic radical having 3 to 13 carbon atoms and 1 to 4 heteroatoms from the group comprising oxygen, sulfur and nitrogen, of which a maximum of 1 is different from nitrogen, in the ring system, unsubstituted or mono- or polysubstituted by
  1) halogen, such as fluorine, chlorine, bromine or iodine,
  2) alkyl having 1 to 3 carbon atoms,
  3) alkyl having 1 to 3 carbon atoms, mono- or polysubstituted by 3.1 halogen, such as fluorine, chlorine, bromine or iodine,
  4) alkoxy having 1 to 3 carbon atoms,
  5) alkoxy having 1 to 3 carbon atoms, mono- or polysubstituted by 5.1 halogen, such as fluorine, chlorine, bromine or iodine,
  6) nitro,
  7) hydroxyl,
  8) carboxyl,
  9) carbamoyl,
  10) an oxo group,
 b) a radical of the formula II,

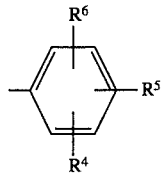

(II)

in which $R^4$, $R^5$ and $R^6$ can be identical or different and are
 1) hydrogen,
 2) alkyl having 1 to 3 carbon atoms,
 3) alkyl having 1 to 3 carbon atoms, mono- or polysubstituted by 3.1 halogen, such as fluorine, chlorine, bromine or iodine,
 4) in which $R^4$ is hydrogen and $R^5$ and $R^6$, together with the phenyl ring of the formula II, form a naphthalene ring,
 5) in which $R^4$ is hydrogen and $R^5$ and $R^6$ form a methylenedioxy radical,
 6) alkoxy having 1 to 3 carbon atoms,
 7) alkoxy having 1 to 3 carbon atoms, mono- or polysubstituted by 7.1 halogen, such as fluorine, chlorine, bromine or iodine,
 8) $(C_1-C_3)$-alkylmercapto,
 9) $(C_1-C_3)$-alkylmercapto, mono- or polysubstituted by 9.1 halogen, such as fluorine, chlorine, bromine or iodine,
 10) halogen, such as fluorine, chlorine, bromine or iodine,
 11) nitro,
 12) cyano,
 13) hydroxyl,
 14) carboxyl,
 15) $(C_1-C_3)$-alkylsulfonyl,
 16) carbalkoxy, having 1 to 3 carbon atoms in the alkyl chain,
 17) benzoyl,
 18) benzoyl, mono- or polysubstituted by 18.1 halogen, such as fluorine, chlorine, bromine or iodine, 18.2 $(C_1-C_3)$-alkyl,
18.3 $(C_1-C_3)$-alkoxy,
19) phenyl,
20) phenyl, mono- or polysubstituted by
   20.1 $(C_1-C_3)$-alkoxy,
   20.2 halogen, such as fluorine, chlorine, bromine or iodine,
   20.3 $(C_1-C_3)$-alkyl,
21) phenoxy,
22) phenoxy, mono- or polysubstituted by
   22.1 $(C_1-C_3)$-alkoxy, mono- or polysubstituted by
      22.1.1 halogen, such as fluorine, chlorine, bromine or iodine,
   22.2 halogen, such as fluorine, chlorine, bromine or iodine,
   22.3 $(C_1-C_3)$-alkyl, mono- or polysubstituted by
      22.3.1 halogen, such as fluorine, chlorine, bromine or iodine,
c) a radical of the formula III,

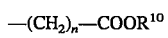   (III)

in which $R^{10}$ is
1) hydrogen
2) alkyl having 1 to 4 carbon atoms, n is an integer from 1 to 12,
d) $R^2$ and $R^3$, together with the nitrogen to which they are bonded, form a 4- to 9-membered ring, substituted by
   1) carbonyl on the carbon atom adjacent to the nitrogen atom,
e) $R^2$ and $R^3$, together with the nitrogen to which they are bonded, form a 5- to 6-membered ring of the formula IV

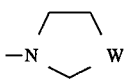   (IV)

in which W is
1) —CH$_2$—,
2) —CH$_2$—CH$_2$—,
3) —CH$_2$—CH—,
         |
         CH$_3$
4) —CH$_2$—CH—,
         |
         C$_2$H$_5$
5) —CH$_2$—CH—,
         |
         OH
6) —CH$_2$—O—
or
7) —CH$_2$—S—

$R^7$ is
a) hydrogen
b) alkyl having 1 to 17 carbon atoms,
c) alkyl having 1 to 3 carbon atoms, mono- or polysubstituted by halogen such as fluorine, chlorine, bromine or iodine,
d) phenyl-$(C_1-C_2)$-alkyl, in particular benzyl;

$R^8$ is
a) hydrogen,
b) methyl,
c) alkenyl having 2 to 3 carbon atoms, for the preparation of pharmaceuticals for the treatment of carcinoses.

Among these pharmaceuticals, the compound 5-methyl-isoxazole-4-carboxylic acid (4-trifluoromethyl)anilide (compound 1) and N-(4-trifluoromethyl)-2-cyano-3-hydroxycrotonamide (compound 2) are preferred.

Suitable physiologically tolerable salts of the compound of the formula I are, for example, alkali metal, alkaline earth metal and ammonium salts including those of organic ammonium bases.

The mono-, di- or trinuclear unsaturated heterocyclic radicals having 3 to 13 carbon atoms include, for example, thienyl, pyridyl, pyrimidinyl, pyrazinyl, pyridazinyl, imidazolyl, thiazolyl, thiazolinyl, oxazolyl, thiadiazolyl, benzoxazolyl, benzimidazolyl, quinolyl, pyrazolyl, acridinyl, indolinyl, tetrazolyl or indazolyl.

The compound of the formula I and its physiologically tolerable salts are particularly suitable for the treatment of a plurality of carcinoses. The types of cancer which are especially inhibited by these compounds include, for example, leukemia, in particular chronic leukemia of the T and B cell type, lymph node cancer, for example Hodgkin's or non-Hodgkin's lymphoma, carcinomas, sarcomas or skin cancer. The active compounds can either be used alone, for example in the form of microcapsules, in mixtures with one another or in combination with suitable auxiliaries and/or excipients.

The compounds of the formula I, Ia or Ib are prepared in a known manner (DE 2,524,959; DE 2,655,009; DE 3,405,727; DE 2,524,929; DE 2,555,789; DE 2,557,003).

The compounds of the formula I, Ia or Ib can be prepared by reacting a compound of the formula V,

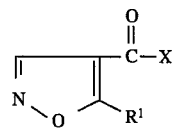   (V)

in which X is a halogen atom, preferably chlorine or bromine, and $R^1$ has the meaning indicated in formula I, with the amine of the formula VI

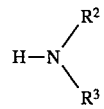   (VI)

in which $R^2$ and $R^3$ has the meaning indicated in formula I, or b) treating a compound of the formula VI

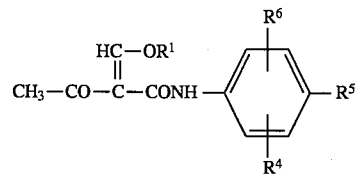

in which $R^4$ is $(C_1-C_4)$-alkyl and $R^4$, $R^5$ and $R^6$ have the meaning indicated in formula I, with expediently an at least equimolar amount of hydroxylamine in an organic solvent, or c) reacting a compound of the formula V, in which X and $R^4$ have the abovementioned meaning, with a primary aliphatic amine of the formula VII

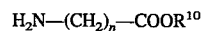   (VII)

in which n and $R^{10}$ have the meaning indicated in formula I, or d) reacting a compound of the formula V, in which X and $R^4$ have the abovementioned meaning, with a lactam of the formula VIII

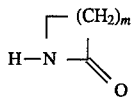  (VIII)

in which m is an integer from 1 to 6, or e) reacting a compound of the formula V, in which X and $R^4$ have the abovementioned meaning, with an amine of the formula IX,

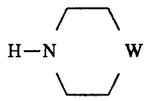  (IX)

in which W has the meaning indicated for formula I, or f) reacting the compound of the formula I in the presence of a basic agent to give the corresponding compound of the formula Ia or Ib.

The invention further relates to novel compounds of the formula I

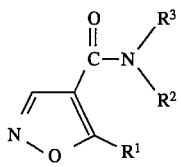  (I)

their possible stereoisomeric forms and/or, if appropriate, their physiologically tolerable salts, where $R^4$ is
  a) hydrogen,
  b) alkyl having 2 to 6 carbon atoms,
  c) alkyl having 1 to 4 carbon atoms, mono- or polysubstituted by
    1) halogen, such as fluorine, chlorine, bromine or iodine,
  d) phenyl, $R^2$ is
  a) hydrogen,
  b) alkenyl having 2 to 3 carbon atoms,
  c) benzyl, $R^3$ is
  a) pyridyl, mono- or polysubstituted by
    1) hydrogen,
    2) halogen, such as fluorine, chlorine, bromine or iodine,
    3) nitro,
    4) alkyl having 1 to 3 carbon atoms,
    5) alkoxy having 1 to 3 carbon atoms,
  b) a radical of the formula II,

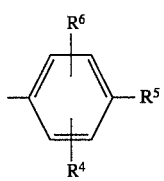  (II)

in which $R^4$, $R^5$ and $R^6$ can be identical or different and are
  1) halogen, such as fluorine, chlorine, bromine or iodine,
  2) nitro,
  3) hydrogen,
  4) benzoyl, mono- or polysubstituted by
    4.1 halogen, such as fluorine, chlorine, bromine or iodine,
    4.2 methyl,
    4.3 methoxy,
  5) $(C_1-C_3)$-alkoxy, mono- or polysubstituted by
    5.1 halogen, such as fluorine, chlorine, bromine or iodine,
  6) $(C_1-C_4)$-alkyl, mono- or polysubstituted by
    6.1 halogen, such as fluorine, chlorine, bromine or iodine,
  7) hydroxyl,
  8) alkylsulfonyl, having 1 to 3 carbon atoms in the alkyl chain,
  9) in which $R^4$ is hydrogen and $R^5$ and $R^6$ together form a methylenedioxy radical,
  10) cyano,
  11) $(C_1-C_3)$-alkylmercapto,
  12) benzoyl,
  13) $(C_1-C_3)$-alkyl,
  c) pyrimidinyl, mono- or polysubstituted by
    1) alkyl having 1 to 3 carbon atoms,
  d) indolyl
  e) indazolinyl.

The invention further relates to novel compounds of the formula Ia or the formula Ib,

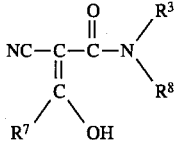  (Ia)

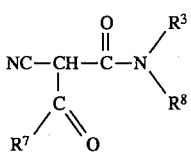  (Ib)

their possible stereoisomeric forms and/or, if appropriate, their physiologically tolerable salts, where the radicals $R^4$, $R^7$ and $R^5$ are the following a) where $R^7$ is
  1) hydrogen,
  2) alkyl having 2 to 4 carbon atoms
  where $R^8$ is
  1) hydrogen,
  2) methyl
  where $R^3$ is
  1) phenyl
  2) phenyl, mono- or polysubstituted by
    2.1 halogen,
    2.2 alkyl having 1 to 3 carbon atoms, mono- or polysubstituted by halogen, such as fluorine, chlorine, bromine or iodine, b) where $R^7$ is
  1) alkyl having 1 to 4 carbon atoms,
  2) hydrogen,
  3) $CF_3$,
  where $R^5$ is
  1) hydrogen,
  2) methyl,
  3) alkenyl having 2 to 3 carbon atoms,
  where $R^3$ is 1) pyridyl,
2) pyridyl, mono- or polysubstituted by
   2.1 halogen, such as fluorine, chlorine, bromine or iodine,
   2.2 alkyl having 1 to 3 carbon atoms,
3) pyrimidinyl, substituted as for 2)
4) thiazolyl, substituted as for 2) and 4.1 alkoxycarbonyl, having 1 to 3 carbon atoms in the alkyl chain,
5) benzothiazolyl, substituted as for 2),
6) benzimidazolyl, substituted as for 2),
7) indazolyl, substituted as for 2),
8) phenyl, mono- or polysubstituted by
   8.1 benzoyl,
   8.2 benzoyl, mono- or polysubstituted by
      8.2.1 halogen, such as fluorine, chlorine, bromine or iodine,
      8.2.2 alkyl having 1 to 3 carbon atoms,
      8.2.3 alkoxy having 1 to 3 carbon atoms,
      8.2.4 alkoxy having 1 to 3 carbon atoms, mono- or polysubstituted by halogen such as fluorine, chlorine, bromine or iodine,
   8.3 carboxyl,
   8.4 hydroxyl,
c) where $R^7$ is
   1) hydrogen,
   2) alkyl having 1 to 4 carbon atoms,
   where $R^8$ is
   1) hydrogen,
   2) methyl,
   where $R^3$ is
   1) a radical of the formula III $$-(CH_2)_4-COOR^{10}$$

in which $R^{10}$ is
   1.1 hydrogen
   1.2 alkyl having 1 to 4 carbon atoms,
d) where $R^7$ is
   1) hydrogen,
   2) alkyl having 1 to 4 carbon atoms,
   $R^8$ and $R^3$, together with the nitrogen to which they are bonded, form a 4- to 9-membered ring, substituted by
   2.1 carbonyl on the carbon atom adjacent to the nitrogen atom,
or
   $R^8$ and $R^3$, together with the nitrogen to which they are bonded, form a piperidine ring optionally substituted by alkyl having 1 to 3 carbon atoms.

The invention also further relates to the use of the novel compounds of the formula I, Ia or Ib and/or at least one of their physiologically tolerable salts for the production of pharmaceuticals for the prophylaxis and/or treatment of rheumatic disorders.

The invention also relates to pharmaceuticals which consist of at least one compound of the formula I and/or at least one of its physiologically tolerable salts or contain at least one of these active compounds in addition to pharmaceutically suitable and physiologically tolerable excipients, diluents and/or other auxiliaries.

The pharmaceuticals according to the invention can be administered orally, topically, rectally, if desired, also parenterally, oral administration being preferred.

Suitable solid or liquid pharmaceutical preparation forms are, for example, granules, powders, coated tablets, tablets, (micro)capsules, suppositories, syrups, elixirs, suspensions, emulsions, drops or injectable solutions and also preparations having sustained release of active compound, in whose production are used customary auxiliaries, such as excipients, disintegrants, binders, coating agents, swelling agents, glidants or lubricants, flavorings, sweetening agents or solubilizers. Frequently used auxiliaries which may be mentioned are, for example, magnesium carbonate, titanium dioxide, lactose, mannitol and other sugars, talc, lactoprotein, gelatin, starch, cellulose and its derivatives, animal and vegetable oils, polyethylene glycols and solvents, such as, for example, sterile water and mono- or polyhydric alcohols, for example glycerol.

The pharmaceutical preparations are preferably produced and administered in dosage units, each unit containing a certain dose of at least one of the compound of the formula I and/or of at least one of their physiologically tolerable salts as the active constituent. In the case of solid dosage units, such as tablets, capsules, coated tablets or suppositories, this dose can be up to about 300 mg, but preferably about 10 to 50 mg.

For the treatment of an adult patient (70 kg) suffering from leukemia—depending on the activity of the compounds of the formula I and/or their physiologically tolerable salts in humans—daily doses of about 5 to 300 mg of active compound, preferably about 25 to 100 mg, are indicated in the case of oral administration. Under certain circumstances, however, higher or lower daily doses may also be appropriate. The daily dose can be administered both by means of a single administration in the form of an individual dosage unit or else of several smaller dosage units and also by means of a multiple administration of subdivided doses at specific intervals.

Finally, the compounds of the formula I and/or at least one of their physiologically tolerable salts can also be formulated together with other suitable active compounds, for example other antitumor agents, immunoglobulins, monoclonal antibodies, immunostimulating agents or antibiotics, for the production of the abovementioned pharmaceutical preparation forms. These compounds can also be administered in accompaniment to a radiation therapy.

Pharmacological tests and results

The cell culture in vitro proliferation test was used as an activity test for chemotherapeutics.

EXAMPLE 1

Proliferation test

Clicks/RPMI 1640 medium (50:50) containing L-glutamine without any $NaHCO_3$, in the form of powder for 10 l (Seromed, Biochrom, Berlin, FRG) is dissolved in 9 l of double-distilled water, and sterile filtered into 900 ml bottles.

Washing medium 900 ml of base medium are buffered using 9.5 ml of 7.5% strength sodium hydrogencarbonate solution and 5 ml of HEPES (N-2-hydroxyethyl-piperazine-N-2 ethanesulfonic acid) (Gibco, Eggenstein, FRG).

Working medium 900 ml of base medium plus 19 ml of $NaHCO_3$ solution (7.5%; 10 ml of HEPES solution and 10 ml of L-glutamine solution (200 mM)).

Medium for mitogen-induced lymphocyte proliferation.

Working medium containing 1% heat-inactivated (30 min, 56° C.) fetal calf serum (FCS) is prepared.

Tumor cell medium

For keeping the tumor cells and hybridoma cells, working medium containing 5% FCS is prepared.

Culture medium for cell lines

For keeping the cell lines, 900 ml of working medium are mixed with 10% FCS, 10 ml of NEA (non-essential amino acids) solution (Gibco), 10 ml of sodium pyruvate solution (100 mM, Gibco) and 5 ml of $10^{-2}$M mercaptoethanol.

Preparation and working-up of the spleen cells for mitogen-induced lymphocyte proliferation The mice are sacrificed by cervical dislocation and the spleens are removed under sterile conditions. The spleens are shredded on a sterile sieve having a mesh width of 80 "mesh" and are carefully transferred to a Petri dish containing working medium using the plunger of a plastic syringe (10 ml). To remove the erythrocytes from the spleen cell suspension, the mixture is incubated at room temperature for about 1 min, with occasional shaking, in hypotonic 0.17M ammonium chloride solution. The erythrocytes are lysed in the course of this, while the viability and reactivity of the lymphocytes is not influenced. After centrifugation (7 min/ 340 g), the lysate is discarded, and the cells are washed twice and then taken up in the respective test medium.

Mitogen-induced lymphocyte proliferation $5 \times 10^5$ worked-up spleen cells from female NMRI mice in 200 μl of test medium per well were pipetted into flat bottom microtiter plates together with various mitogens and preparations. The following mitogen and preparation concentrations were used:

concanavalin A [Serva]: 0.5–0.25–0.12 μg/ml lipopolysaccharide [Calbiochem]: 1.0–0.5–0.1 μg/ml phytohemagglutinin [Gibco]: 0.5–0.25–0.12% stock solution pokeweed mitogen [Gibco] compound 1 or 2: 50, 25, 10, 7.5, 5, 2.5, 1, 0.5, 0.1 μmol The group with mitogen additions and without preparation were defined as positive controls. The negative controls were cells in culture medium containing preparation without mitogen additions. Each mitogen concentration was tested four times with all preparation concentrations. After incubation at 37° C./5% $CO_2$ for 48 hours, 25 μl/well of tritium thymidine (Amersham) having an activity of 0.25 μCi/well ($9.25 \times 10^3$ Bq) are added to the cells. A further incubation follows, under the same conditions, for a period of 16 h. To evaluate the test batch, the cells are harvested on filter paper by means of a cell harvesting apparatus (Flow Laboratories), unincorporated thymidine being collected in a separate waste bottle. The filter paper is dried, punched out and added together with 2 ml of scintillator (Rotiszint 22, Roth) to vials which are then cooled to 4° C. for a further 2 h. The amount of radioactivity incorporated by these cells is measured in a beta counter (Packard, Tricarb 460c).

Preparation of the tumor cells and cell lines for the proliferation test

The tumor cells or cell lines used in the test are taken from the main stock in the logarithmic growth phase, washed twice with washing medium and suspended in the appropriate medium.

Carrying-out and evaluation of the proliferation tests

The proliferation test was carried out in round bottom microtiter plates. Compound 1 and interleukins were each dissolved in 50 μl/well of the appropriate medium and the cell number ($5 \times 10^5$) was set using 100 μl/well so that a final volume of 200μl well results. In all tests, the values were determined four times. Cells without preparation and without growth factor were defined as the negative control and cells without preparation and with growth factor gave the values for the positive control. The value of the negative control was subtracted from all values determined and the difference of positive control minus negative control was set at 100%. The plates were incubated at 37° C./5% $CO_2$ for 72 h and the proliferation rate was determined correspondingly as with the mitogen-induced lymphocyte proliferation.

The cell lines were taken from the strain collection, American Type Culture Collection (ATCC).

Table 1 shows the concentrations at which a 50% inhibition occurs:

TABLE 1

| Cell line | Origin | $ED_{50}$ |
|---|---|---|
| CTLL | mouse T cell line ($T_c$ clone IL-2) | 40–50 μm |
| HT-2 | mouse T cell line (IL-2) | 40–50 μm |
| CTL-J-K | mouse T cell line ($T_c$, IL-2) | 40–50 μm |
| Cl 9/4 | mouse T cell line (IL-4 dep.) | 25 μm |
| K III 5 | mouse T cell line ($T_h$, IL-2) | 1–3 μm |
| Spleen T | mouse (con A and PWM) | 10 μm |
| Spleen B | mouse (LPS) | 10 μm |
| A20 2J | mouse B cell tumor (BALB/c) | 1–3 μm |
| TRK 4 | mouse B cell hybridoma | 5 μm |
| TRK 5 | mouse B cell hybridoma | 5 μm |
| Bone marrow | mouse (M-CSF, GM CSF) | 5 μm |
| WEHI 279 | mouse B cell lymphoma | ≦1 μm |
| P 388 D1 | mouse Mø tumor | 10 μm |
| 7TD1 | mouse B cell hybridoma (IL-6) | 10 μm |
| G53 | mouse T cell clone | |
| PB-3C | mouse mast cell line (IL-3) | 20 μm |
| DA-1 | mouse tumor (IL-3) | 5 μm |
| 7D4 | rat hybridoma | ≦1 μm |
| A431 | human epidermoid carcinoma | 15 μm |
| KB | human epidermoid carcinoma | 15 μm |
| HFF | human foreskin fibroblast | 40 μm |
| HL-60 | human promyelomonocytic leukemia | 25 μm |

EXAMPLE 2

Acute toxicity on oral administration

Compound 1 was administered orally to the mice or rats to determine the acute toxicity.

The $LD_{50}$ values were determined according to Litchfield and Wilcoxon.

The weight of the NMRI mice (NMRI: Naval Medical Research Institute) is 20 to 25 g and that of the SD rats (SD: Sprague-Dawley) is 120 to 165 g. The mice were fasted for about 18 hours before the test. They are fed normally again 5 hours after administration of the substances tested. After 3 weeks, the animals were sacrificed by means of chloroform and dissected. 6 animals are used per dose. The results are summarized in Table 2.

TABLE 2

| | Compound 1 Acute toxicity Oral $LD_{50}$ (mg/kg) | | Compound 2 Acute toxicity Oral $LD_{50}$ (mg/kg) |
|---|---|---|---|
| NMRI mouse | 445 (362–546) | SD rat | 160 (133–193) |
| SD rat | 235 (167–332) | | |

EXAMPLE 3

Acute toxicity after intraperitoneal administration

The acute toxicity after intraperitoneal administration of the test substances was carried out using NMRI mice (20 to 25 g) and SD rats (120 to 195 g). The test substance was suspended in a 1% strength sodium carboxymethyl cellulose solution. The various doses of the test substance were administered to the mice in a volume of 10 ml/kg of body weight and to the rats in a volume of 5 ml/kg of body weight. 10 animals were used per dose. After 3 weeks, the acute toxicity was determined according to the method of Litchfield and Wilcoxon. The results are summarized in Table 3.

TABLE 3

| | Compound 1 acute toxicity intraperitoneal LD$_{50}$ (mg/kg) | | Compound 2 acute toxicity intraperitoneal LD$_{50}$ (mg/kg) |
|---|---|---|---|
| NMRI mouse | 185 (163–210) | NMRI mouse | (100–200) |
| SD rat | 170 (153–189) | | |

EXAMPLE 4

A Preparation of 5-methylisoxazole-4-carboxylic acid (4-trifluoromethyl)anilide

A solution of 0.05 mol of 5-methylisoxazole-4-carbonyl chloride (7.3 g) in 20 ml of acetonitrile is added dropwise at room temperature to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile each time and the combined filtrates are concentrated under reduced pressure. 12.8 g of white crystalline 5-methylisoxazole-4-carboxylic acid (4-trifluoromethyl)-anilide (compound 1) are thus obtained.

B Preparation of N-(4-trifluoromethylphenyl)-2-cyano-3-hydroxycrotonamide 0.1 mol of 5-methylisoxazole-4-carboxylic acid (4-trifluoromethyl)anilide is dissolved in 100 ml of methanol and a solution of 0.11 mol (4.4 g) of sodium hydroxide solution in 100 ml of water is added at +10° C. The mixture is stirred for 30 minutes and acidified with concentrated hydrochloric acid after diluting with water. The precipitated crystal magma is filtered off with suction, washed with water and dried in the air. The yield is 24.4 g of N-(4-trifluoromethylphenyl)-2-cyano-3-hydroxycrotonamide (compound 2).

Melting point from methanol 205° to 206° C.
Preparation examples

The structure of all compounds described below was checked by means of elemental analysis and IR and $^1$H-NMR spectra.

5. N-(4-chlorodifluoromethoxy)phenyl-5-ethylisoxazole-4-carboxamide

A solution of 0.05 mol (7.3 g) of 5-methylisoxazole-4-carbonyl chloride in 30 ml of acetonitrile is added dropwise at room temperature with stirring to 0.1 mol (19.4 g) of 4-chlorodifluoromethoxyaniline, dissolved in 180 ml of acetonitrile. The mixture is stirred for a further 20 minutes and the liquid is filtered off from the precipitated salt. The filtrate is brought to dryness under reduced pressure. 28.5 g (94.2% of th.) of crystalline product are thus obtained.

Melting point [from cyclohexane acetone 20:1 (v/v)]: 112°–113° C.

The following compounds of the formula I are prepared analogously to the example described above.

6. N-(4-fluorophenyl)isoxazole-4-carboxamide [of melting point 162° to 164° C.) from isoxazole-4-carbonyl chloride and 4-fluoroaniline.
7. N-(4-chlorophenyl)isoxazole-4-carboxamide [of melting point 175° to 177° C. (dec.)] from isoxazole-4-carbonyl chloride and 4-chloroaniline.
8. N-(4-bromophenyl)isoxazole-4-carboxamide [of melting point 184° to 186° C. (dec.)] from isoxazole-4-carbonyl chloride and 4-bromoaniline.
9. N-(4-iodophenyl)isoxazole-4-carboxamide [of melting point 207° to 208° C. (dec.)] from isoxazole-4-carbonyl chloride and 4-iodoaniline.
10. N-(4-nitrophenyl)isoxazole-4-carboxamide [of melting point 208° to 210° C. (dec.)] from isoxazole-4-carbonyl chloride and 4-nitroaniline.
11. N-(3,4-methylenedioxyphenyl)isoxazole-4-carboxamide (of melting point 168° to 169° C.) from isoxazole-4-carbonyl chloride and 3,4-methylene-dioxyaniline.
12. N-(4-benzoylphenyl)isoxazole-4-carboxamide [of melting point 197° to 199° C. (dec.)] from isoxazole-4-carbonyl chloride and 4-aminobenzophenone.
13. N-(4-fluorophenyl)-5-ethylisoxazole-4-carboxamide (of melting point 75° to 77° C.) from 5-ethylisoxazole-4-carbonyl chloride and 4-fluoroaniline.
14. N-(4-chlorophenyl)-5-ethylisoxazole-4-carboxamide (of melting point 103° to 105° C.) from 5-ethylisoxazole-4-carbonyl chloride and 4-chloroaniline.
15. N-(4-bromophenyl)-5-ethylisoxazole-4-carboxamide (of melting point 117° to 118° C.) from 5-ethylisoxazole-4-carbonyl chloride and 4-bromoaniline.
16. N-(4-nitrophenyl)-5-ethylisoxazole-4-carboxamide (of melting point 139° to 141° C.) from 5-ethylisoxazole-4-carbonyl chloride and 4-nitroaniline.
17. N-(3,4-methylenedioxyphenyl)-5-ethylisoxazole-4-carboxamide (of melting point 105° to 106° C.) from 5-ethylisoxazole-4-carbonyl chloride and 3,4-methylene-dioxyaniline.
18. N-(4-trifluoromethoxyphenyl)-5-ethylisoxazole-4-carboxamide (of melting point 52° to 54° C.) from 5-ethylisoxazole-4-carboxamide and 4-trifluoromethoxyaniline.
19. N-(4-benzoylphenyl)-5-ethylisoxazole-4-carboxamide (of melting point 168° to 170° C.) from 5-ethylisoxazole-4-carbonyl chloride and 4-aminobenzophenone.
20. N-[4-(4-fluorobenzoyl)phenyl]-5-ethylisoxazole-4-carboxamide (of melting point 153° to 155° C.) from 5-ethylisoxazole-4-carboxamide and 4-(4-fluorobenzoyl)aniline.
21. N-[4-(4-chlorobenzoyl)phenyl],5-ethylisoxazole-4-carboxamide (of melting point 159° to 161° C.) from 5-ethylisoxazole-4-carbonyl chloride and 4-(4-chlorobenzoyl)aniline.
22. N-[4-(4-bromobenzoyl)phenyl]-5-ethylisoxazole-4-carboxamide (of melting point 178° to 181° C.) from 5-ethylisoxazole-4-carbonyl chloride and 4-(4-bromobenzoyl)aniline.
23. N-(4-benzoylphenyl)-5-propylisoxazole-4-carboxamide (of melting point 134° to 135° C.) from 5-propylisoxazole-4-carbonyl chloride and 4-aminobenzophenone.
24. N-(4-chlorophenyl)-5-butylisoxazole-4-carboxamide (of melting point 91° to 92° C.) from 5-butylisoxazole-4-carbonyl chloride and 4-chloroaniline.
25. N-(4-benzoylphenyl)-5-butylisoxazole-4-carboxamide (of melting point 108° to 110° C.) from 5-butylisoxazole-4-carbonyl chloride and 4-amino-benzophenone.
26. N-(4-fluorophenyl)-5-trifluoromethylisoxazole-4-carboxamide (of melting point 97° C.) from 5-trifluoromethylisoxazole-4-carbonyl chloride and 4fluoroaniline.
27. N-(4-chlorophenyl)-5-trifluoromethylisoxazole-4-carboxamide (of melting point 90° to 92° C.) from 5-trifluoromethylisoxazole-4-carbonyl chloride and 4chloroaniline.
28. N-(4-nitrophenyl)-5-trifluoromethylisoxazole-4-carboxamide (of melting point 136° to 138° C.) from 5-trifluoromethylisoxazole-4-carbonyl chloride and 4-nitroaniline.
29. N-(3,4-methylenedioxyphenyl)-5-trifluoromethyl-isoxazole-4-carboxamide (of melting point 114° to 116° C.) from 5-trifluoromethylisoxazole-4-carbonyl chloride and 3,4-methylenedioxyaniline.
30. N-(4-trifluoromethylphenyl)-5-chloromethylisoxazole-4-carboxamide (of melting point 136° to 137° C.) from 5-chloromethylisoxazole-4-carbonyl chloride and 4trifluoromethylaniline.

31. N-(4-trifluoromethylphenyl)-5-phenylisoxazole-4carboxamide (of melting point 159° to 160° C.) from 5-phenylisoxazole-4-carbonyl chloride and 4-trifluoromethylaniline.
32. N-(4-fluorophenyl)-5-phenylisoxazole-4-carboxamide (of melting point 151° to 153° C.) from 5-phenyl-isoxazole-4-carbonyl chloride and 4-fluoroaniline.
33. N-(4-methylsulfonylphenyl)-5-methylisoxazole-4-carboxamide (of melting point 170° to 172° C.) from 5-methylisoxazole-4-carbonyl chloride and 4-methylsulfonylaniline.
34. N-benzyl-N-(4-trifluoromethylphenyl)-5-methylisoxazole-4-carboxamide (of melting point 87° to 89° C.) from 5-methylisoxazole-4-carbonyl chloride and N-benzyl-4-trifluoromethylaniline.
36. N-(5-chloro-2-pyridyl)isoxazole-4-carboxamide (of melting point 254° to 255° C.) from isoxazole-4-carbonyl chloride and 2-amino-5-chloropyridine.
37. N-(5-chloro-2-pyridyl)-5-ethylisoxazole-4-carboxamide (of melting point 133° to 136° C.) from 5-ethylisoxazole-4-carbonyl chloride and 2-amino-5-chloropyridine.
38. N-(5-bromo-2-pyridyl)-5-ethylisoxazole-4-carboxamide (of melting point 144° to 145° C.) from 5-ethylisoxazole-4-carbonyl chloride and 2-amino-5-bromopyridine.
39. N-(5-nitro-2-pyridyl)-5-ethylisoxazole-4-carboxamide (of melting point 236° to 237° C.) from 5-ethylisoxazole-4-carbonyl chloride and 2-amino-5-nitropyridine.
40. N-(5-chloro-2-pyridyl)-5-phenylisoxazole-4-carboxamide (of melting point 160° to 161° C.) from 5-phenylisoxazole-4-carbonyl chloride and 2-amino-5-chloropyridine.
41. N-(5-indolyl)-5-methylisoxazole-4-carboxamide (of melting point 155° to 157° C.) from 5-methylisoxazole-4-carbonyl chloride and 5-aminoindole.
42. N-(6-indazolyl)-5-methylisoxazole-4-carboxamide (of melting point 198° to 202° C.) from 5-methylisoxazole-4-carbonyl chloride and 6-aminoindazole.
43. N-(5-indazolyl)-5-methylisoxazole-4-carboxamide (of melting point 218° to 220° C.) from 5-methylisoxazole-4-carbonyl chloride and 5-aminoindazole.
44. N-allyl-N-phenyl-5-methylisoxazole-4-carboxamide (of melting point 79° to 85° C.) from 5-methylisoxazole-4-carbonyl chloride and N-allylaniline.
45. N-[3-(1,1,2,2-tetrafluoroethoxy)phenyl]-5-methyl-isoxazole-4-carboxamide (of melting point 97° C.) from 5-methylisoxazole-4-carbonyl chloride and 3-(1,1,2,2-tetrafluoroethoxy)aniline.
46. N-(4-cyanophenyl)-5-methylisoxazole-4-carboxamide (of melting point 197° to 200° C.) from 5-methylisoxazole-4-carbonyl chloride and 4-cyanoaniline.
47. N-(4-methylmercaptophenyl)-5-methylisoxazole-4carboxamide (of melting point 134° to 136° C.) from 5-methylisoxazole-4-carbonyl chloride and 4-methylmercaptoaniline.
48. N-(4,6-dimethyl-2-pyridyl)-5-methylisoxazole-4-carboxamide (of melting point 210° C.) from 5-methylisoxazole-4-carbonyl chloride and 2-amino-4,6-dimethylpyridine.
49. N-(4,6-dimethyl-2-pyrazinyl)-5-methylisoxazole-4-carboxamide (of melting point 222° to 226° C.) from 5-methylisoxazole-4-carbonyl chloride and 2-amino-4,6-dimethylpyrazine.
50. N-(4-trifluoromethoxyphenyl)-2-cyano-3-hydroxycrotonamide 0.1 mol (28.6 g) of N-(4-trifluoromethoxyphenyl)-5-methylisoxazole-4-carboxamide is dissolved in 100 ml of ethanol and a solution of 0.11 mol (4.4 g) of sodium hydroxide solution in 100 ml of water is added at 20° C. The mixture is stirred for 30 minutes and acidified with concentrated hydrochloric acid after diluting with water. The precipitated crystal magma is filtered off with suction, washed with water and dried in the air. 27.7 g (9.1% of theory) of N-(4-trifluoromethoxyphenyl)-2-cyano-3-hydroxycrotonamide of melting point 171°–176° C. (from ethanol) are thus obtained.

The following compounds of the formula Ia or Ib are prepared analogously to the example described above.
51. 2-cyano-3-hydroxy-N-[4-(1,1,2,2-tetrafluoroethoxy)phenyl]crotonamide (of melting point 166°–164° C.) from N-[4-(1,1,2,2,-tetrafluoroethoxy)phenyl]-5-methylisoxazole-4-carboxamide.
52. N-(5-chloro-2-pyridyl)-2-cyano-3-hydroxycrotonamide [(of melting point 213° to 215° C. (dec.)] from N-(5-chloro-2-pyridyl)-5-methylisoxazole-4-carboxamide.
53. N-(2-chloro-3-pyridyl)-2-cyano-3-hydroxycrotonamide (of melting point 128° to 131° C.) from N-(2-chloro-3-pyridyl)-5-methylicoxazole-4-carboxamide.
54. N-(4-benzoylphenyl)-2-cyano-3-hydroxycrotonamide (of melting point 186° to 188° C.) from N-(4-benzoylphenyl)-5-methylisoxazole-4-carboxamide.
55. N-[4-(4-chlorobenzoyl)phenyl]-2-cyano-3-hydroxy-4-methylcrotonamide (of melting point 157° to 159° C.) from N-[4-(4-chlorobenzoyl)phenyl]-5-ethylisoxazole-4-carboxamide.
56. N-[4-(4-bromobenzoyl)phenyl]-2-cyano-3-hydroxycrotonamide (of melting point 221° to 223° C.) from N-[4-(4-bromobenzoyl)phenyl]-5-methylisoxazole-4-carboxamide.
57. N-[4-(4-methoxybenzoyl)phenyl-2-cyano-3-hydroxycrotonamide (of melting point 74° to 75° C.) from N-[4-(4-methoxybenzoyl)phenyl]-5-methylisoxazole-4-carboxamide.
58. N-(4-(4-methylbenzoyl)phenyl]-2-cyano-3-hydroxycrotonamide (of melting point 177° to 179° C.) from N-[4-(4-methylbenzoyl)phenyl]-5-methylisoxazole-4-carboxamide.
59. N-(5-chloro-2-pyridyl)-2-cyano-3-hydroxy-4-methylcrotonamide (of melting point 206° to 208° C.) from N-(5-chloro-2-pyridyl)-5-ethylisoxazole-4-carboxamide.
60. N-(5-bromo-2-pyridyl)-2-cyano-3-hydroxy-4-methylcrotonamide [of melting point 200° to 202° C. (dec.)] from N-(5-bromo-2-pyridyl)-5-ethylisoxazole-4-carboxamide.
61. 2-cyano-3-hydroxy-4-methyl-N-(4-nitrophenyl)-crotonamide [of melting point 202° to 203° C. (dec.)] from N-(4-nitrophenyl)-5-ethylisoxazole-4-carboxamide.
62. N-(3,4-methylenedioxyphenyl)-2-cyano-3-hydroxy-4-methylcrotonamide (of melting point 99° to 100° C.) from N-(3,4-methylenedioxyphenyl)-5-ethylisoxazole-4-carboxamide.
63. N-(4-benzoylphenyl)-2-cyano-3-hydroxy-4-propylcrotonamide from N-(4-benzoylphenyl)-5-butylisoxazole-4-carboxamide.
64. N-(5-bromo-2-pyridyl)-2-cyano-3-hydroxycrotonamide [of melting point 220° to 223° C. (dec.)] from N-(5-bromo-2-pyridyl)-5-methylisoxazole-4-carboxamide.
65. N-[4-(4-chlorobenzoyl)phenyl]-2-cyano-3-hydroxycrotonamide [of melting point 219° to 223° C. (dec.)] from N-[4-(4-chlorobenzoyl)phenyl]-5-methylisoxazole-4-carboxamide.
66. N-[4-(4-fluorobenzoyl)phenyl]-2-cyano-3-hydroxycrotonamide [of melting point 229° to 231° C. (dec.)] from N-[4-(4-fluorobenzoyl)phenyl]-5methylisoxazole-4-carboxamide.
67. N-[4-(4-fluorobenzoyl) phenyl]-2-cyano-4-methyl-3-hydroxycrotonamide (of melting point 147° to 148° C.) from N-[4-(4-fluorobenzoyl)phenyl]-5-ethylisoxazole-4-carboxamide.

68. N-[4-(4-bromobenzoyl)phenyl]-2-cyano-3-hydroxy-4-methylcrotonamide (of melting point 153° to 155° C.) from N-[4-(4-bromobenzoyl)phenyl]-5-ethylisoxazole-4-carboxamide.
69. N-(4-trifluoromethoxy)phenyl-2-cyano-3-hydroxy-4-methylcrotonamide (of melting point 166° to 167° C.) from N-(4-trifluoromethoxy)phenyl-5-ethylisoxazole-4-carboxamide.
70. N-(4-fluorophenyl)-2-cyano-3-hydroxy-4-methylcrotonamide (of melting point 145° C.) from N-(4-fluorophenyl)-5-ethylisoxazole-4-carboxamide.
71. N-(3,4-methylenedioxyphenyl)-2-cyano-3-hydroxy-4-methylcrotonamide (of melting point 99° to 100° C.) from N-(3,4-methylenedioxyphenyl)-5-ethylisoxazole-4-carboxamide.
72. N-(4-methylsulfonyl)phenyl-2-cyano-3-hydroxycrotonamide (of melting point 196° to 198° C.) from N-(4-methylsulfonyl)phenyl-5-methylisoxazole-4-carboxamide.
73. N-allyl-N-phenyl-2-cyano-3-hydroxycrotonamide (of melting point 57° to 50° C.) from N-allyl-N-phenyl-5-methylisoxazole-4-carboxamide.
74. N-(4-ethoxycarbonylmethyl-2-thiazolyl)-2-cyano-3-hydroxycrotonamide (of melting point 147° C.) from N-(4-ethoxycarbonylmethyl-2-thiazolyl)-5-methylisoxazole-4-carboxamide.
75. N-(2-benzimidazolyl)-2-cyano-3-hydroxycrotonamide (of decomposition point>300° C.) from N-(2-benzimidazolyl)-5-methylisoxazole-4-carboxamide.
76. N-(4-methyl-2-thiazolyl)-2-cyano-3-hydroxycrotonamide [of melting point 210° to 212° C. (dec.)] from N-(4-methyl-2-thiazolyl)-5-methylisoxazole-4-carboxamide.
77. N-(4-chloro-2-benzothiazolyl)-2-cyano-3-hydroxycrotonamide [of melting point 211° to 213° C. (dec.)] from N-(4-chloro-2-benzothiazolyl)-5-methylisoxazole-4-carboxamide.
78. N-(3-pyridyl)-2-cyano-3-hydroxycrotonamide [of melting point 240° to 250° C. (dec.)] from N-(3-pyridyl)-5-methylisoxazole-4-carboxamide.
79. N-(4,6-dimethyl-2-pyridyl)-2-cyano-3-hydroxycrotonamide (of melting point 184° to 186° C.) from N-(4,6-dimethyl-2-pyridyl)-5-methylisoxazole-4-carboxamide.
80. N-(4,6-dimethyl-2-pyrimidyl)-2-cyano-3-hydroxycrotonamide (of melting point 221°) from N-(4,6-dimethyl-2-pyrimidyl)-5-methylisoxazole-4-carboxamide.
81. N-(6-indazolyl)-2-cyano-3-hydroxycrotonamide (of melting point>300° C.) from N-(6-indazolyl)-5-methylisoxazole-4-carboxamide.
82. N-(5-indazolyl)-2-cyano-3-hydroxycrotonamide (of melting point 220° to 223° C.) from N-(5-indazolyl)-5-methylisoxazole-4-carboxamide.
83. N-(4-carboxy-3-hydroxyphenyl)-2-cyano-3-hydroxycrotonamide [of melting point 242° to 246° C. (dec.)] from N-(4-carboxy-3-hydroxyphenyl)-5-methylisoxazole-4-carboxamide
84. N-(3-carboxy-4-hydroxyphenyl)-2-cyano-3-hydroxycrotonamide [of melting point 248° to 252° C. (dec.)] from N-(3-carboxy-4-hydroxyphenyl)-5-methylisoxazole-4-carboxamide
85. N-(4-carboxy-3-chlorophenyl)-2-cyano-3-hydroxycrotonamide [of melting point 218° to 224° C. (dec.)] from N-(4-carboxy-3-chlorophenyl)-5-methylisoxazole-4-carboxamide
86. N-(4-hydroxyphenyl)-2-cyano-3-hydroxycrotonamide [of decomposition point 184° to 186° C. (dec.)] from N-(4-hydroxyphenyl)-5-methylisoxazole-4-carboxamide.
87. N-[4-(4-trifluoromethylphenoxy)phenyl]-2-cyano-3-hydroxy-4-methylcrotonamide (of melting point 147° to 149° C.) from N-[4-(4-trifluoromethylphenoxy)phenyl]-5-ethylisoxazole-4-carboxamide.
88. N-[4-(4-trifluoromethylphenoxy)phenyl]-2-cyano-3-hydroxy-crotonamide (of melting point 171° to 173° C.) from N-[4-(4-trifluoromethylphenoxy)phenyl]-5-methylisoxazole-4-carboxamide.
89. N-methyl-N-(4-trifluoromethylphenyl)-2-cyano-3-hydroxycrotonamide (of melting point 69° to 70° C.) from N-methyl-N-(4-trifluoromethylphenyl)-5-methylisoxazole-4-carboxamide.
90. 2-hydroxyethylidenecyanoacetopiperidide from N-(5-methyl-4-isoxazolylcarbonyl)piperidine.
91. 2-hydroxyethylidenecyanoaceto-4-methylpiperidide from N-(5-methyl-4-isoxazolylcarbonyl)-4-hydroxypiperidine.
92. N-(4-carboxybutyl)-2-cyano-3-hydroxycrotonamide (of melting point 92° C.) from N-(5-methyl- 4-isoxazolylcarbonyl)-5-aminovaleric acid.
93. N-(4-ethoxycarbonylbutyl)-2-cyano-3-hydroxycrotonamide from N-(4-ethoxycarbonylbutyl)-5-methylisoxazole-4-carboxamide.
94. N-(6-carboxyhexyl)-2-cyano-3-hydroxycrotonamide (of melting point 93° to 94° C.) from N-(5-methyl-4-isoxazolylcarbonyl)-7-aminoheptanoic acid.

TABLE 4

Compounds of the formula I

| Example No. | R₁ | R₂ | R₃ |
|---|---|---|---|
| 5 | CH₃ | H | 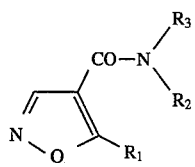—O—CF₂Cl |

TABLE 4-continued
Compounds of the formula I
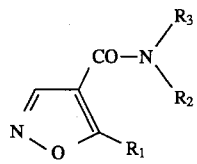
| Example No. | $R_1$ | $R_2$ | $R_3$ |
|---|---|---|---|
| 6 | H | 4-F-C₆H₄ | H |
| 7 | H | H | 4-Cl-C₆H₄ |
| 8 | H | 4-Br-C₆H₄ | H |
| 9 | H | H | 4-I-C₆H₄ |
| 10 | H | 4-NO₂-C₆H₄ | H |
| 11 | H | H | 3,4-methylenedioxyphenyl |
| 12 | H | 4-(PhCO)-C₆H₄ | H |
| 13 | $C_2H_5$ | H | 4-F-C₆H₄ |
| 14 | $C_2H_5$ | 4-Cl-C₆H₄ | H |
| 15 | $C_2H_5$ | H | 4-Br-C₆H₄ |
| 16 | $C_2H_5$ | 4-NO₂-C₆H₄ | H |

TABLE 4-continued
Compounds of the formula I
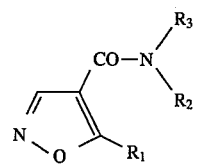
| Example No. | $R_1$ | $R_2$ | $R_3$ |
|---|---|---|---|
| 17 | $C_2H_5$ | H | 3,4-methylenedioxyphenyl |
| 18 | $C_2H_5$ | 4-OCF$_3$-phenyl | H |
| 19 | $C_2H_5$ | H | 4-(C$_6$H$_5$CO)-phenyl |
| 20 | $C_2H_5$ | 4-(4-F-C$_6$H$_4$CO)-phenyl | H |
| 21 | $C_2H_5$ | H | 4-(4-Cl-C$_6$H$_4$CO)-phenyl |
| 22 | $C_2H_5$ | 4-(4-Br-C$_6$H$_4$CO)-phenyl | H |
| 23 | $C_3H_7$ | H | 4-(C$_6$H$_5$CO)-phenyl |
| 24 | $C_4H_9$ | 4-Cl-phenyl | H |
| 25 | $C_4H_9$ | H | 4-(C$_6$H$_5$CO)-phenyl |
| 26 | $CF_3$ | 4-F-phenyl | H |
| 27 | $CF_3$ | H | 4-Cl-phenyl |
| 28 | $CF_3$ | 4-NO$_2$-phenyl | H |

TABLE 4-continued
Compounds of the formula I
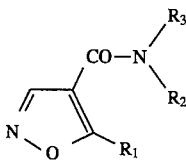
| Example No. | $R_1$ | $R_2$ | $R_3$ |
|---|---|---|---|
| 29 | $CF_3$ | H | 3,4-methylenedioxyphenyl |
| 30 | $CH_2Cl$ | 4-$CF_3$-phenyl | H |
| 31 | phenyl | H | 4-$CF_3$-phenyl |
| 32 | 4-$CF_3$-phenyl | 4-F-phenyl | H |
| 33 | $CH_3$ | H | 4-$SO_2$-$CH_3$-phenyl |
| 34 | $CH_3$ | -$CH_2$-phenyl | 4-$CF_3$-phenyl |
| 36 | H | H | 5-Cl-pyridin-2-yl |
| 37 | $C_2H_3$ | 5-Cl-pyridin-2-yl | H |
| 38 | $C_2H_3$ | H | 5-Br-pyridin-2-yl |
| 39 | $C_2H_5$ | 5-$NO_2$-pyridin-2-yl | H |
| 40 | phenyl | H | 5-Cl-pyridin-2-yl |

TABLE 4-continued

Compounds of the formula I (structure: isoxazole with CO—NR2R3 at 4-position and R1 at 5-position)

| Example No. | R₁ | R₂ | R₃ |
|---|---|---|---|
| 41 | CH₃ | 1H-indol-5-yl | H |
| 42 | CH₃ | H | 1H-benzimidazol-5-yl |
| 43 | CH₃ | 1H-indazol-5-yl | H |
| 44 | CH₃ | —CH₂—CH=CH₂ | phenyl |
| 45 | CH₃ | 3-(O—CF₂—CHF₂)phenyl | H |
| 46 | CH₃ | H | 4-cyanophenyl |
| 47 | CH₃ | 4-(S—CH₃)phenyl | H |
| 48 | CH₃ | H | 2,4,6-trimethylpyridin-3-yl |
| 49 | CH₃ | 2,4,6-trimethylpyrimidin-5-yl | H |

We claim:

1. A method for the treatment of leukemia, sarcomas, carcinoma, lymphoma, or skin cancer comprising the step of administrating a pharmaceutically effective amount of a compound of formula I, Ia, or Ib

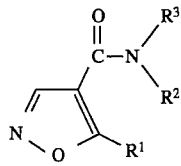   (I)

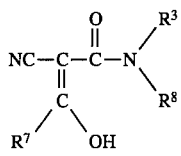   (Ia)

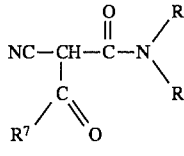   (Ib)

stereoisomeric forms thereof, or physiologically tolerable salts thereof, to a patient in need of such treatment, wherein $R^1$ is
- a) hydrogen,
- b) alkyl having 1 to 6 carbon atoms,
- c) alkyl having 1 to 4 carbon atoms, mono- or polysubstituted by
  - 1) halogen,
- d) phenyl, $R^2$ is
- a) hydrogen,
- b) alkyl having 1 to 4 carbon atoms,
- c) phenyl-$(C_1-C_2)$-alkyl,
- d) alkenyl having 2 to 3 carbon atoms, $R^3$ is
- a) a mono-, di-, or trinuclear, unsaturated heterocyclic radical having 3 to 13 carbon atoms and 1 to 4 heteroatoms from the group comprising oxygen, sulfur, and nitrogen, of which a maximum of 1 is different from nitrogen, in the ring system, unsubstituted or mono- or polysubstituted by
  - 1) halogen
  - 2) alkyl having 1 to 3 carbon atoms,
  - 3) alkyl having 1 to 3 carbon atoms, mono- or polysubstituted by
    - 3.1 halogen,
  - 4) alkoxy having 1 to 3 carbon atoms,
  - 5) alkoxy having 1 to 3 carbon atoms, mono- or polysubstituted by
    - 5.1 halogen,
  - 6) nitro,
  - 7) hydroxyl,
  - 8) carboxyl,
  - 9) carbamoyl,
  - 10) an oxo group,
- b) a radical of the formula II,

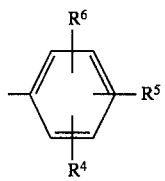   (II)

in which $R^4$, $R^5$, and $R^6$ can be identical or different and are
1) hydrogen,
2) alkyl having 1 to 3 carbon atoms, mono- or polysubstituted by
   2.1 halogen,
3) in which $R^4$ is hydrogen and $R^5$ and $R^6$ together with the phenyl ring of formula II form a naphthalene ring,
4) in which $R^4$ is hydrogen and $R^5$ and $R^6$ form a methylenedioxy radical,
5) alkoxy having 1 to 3 carbon atoms,
6) alkoxy having 1 to 3 carbon atoms, mono- or polysubstituted by
   6.1 halogen,
7) $(C_1-C_3)$-alkylmercapto,
8) $(C_1-C_3)$-alkylmercapto, mono- or polysubstituted by
   8.1 halogen,
9) halogen,
10) nitro,
11) cyano,
12) hydroxyl,
13) carboxyl,
14) $(C_1-C_3)$-alkylsulfonyl,
15) carbalkoxy, having 1 to 3 carbon atoms in the alkyl chain,
16) benzoyl,
17) benzoyl, mono- or polysubstituted by
   17.1 halogen,
   17.2 $(C_1-C_3)$-alkyl,
   17.3 $(C_1-C_3)$-alkoxy,
18) phenyl,
19) phenyl, mono- or polysubstituted by
   19.1 $(C_1-C_3)$-alkoxy,
   19.2 halogen,
   19.3 $(C_1-C_3)$-alkyl,
20) phenoxy,
21) phenoxy, mono- or polysubstituted by
   21.1 $(C_1-C_3)$-alkoxy, mono- or polysubstituted by 21.1.1 halogen,
   21.2 halogen,
   21.3 $(C_1-C_3)$-alkyl, mono- or polysubstituted by
      21.3.1 halogen,
c) a radical of the formula III, $$-(CH_2)_n-COOR^{10}$$   (III)

in which $R^{10}$ is
1) hydrogen
2) alkyl having 1 to 4 carbon atoms, n is an integer from 1 to 12,
d) $R^2$ and $R^3$ together with the nitrogen to which they are bonded, form a 4- to 9-membered ring, substituted by
  1) carbonyl on the carbon atom adjacent to the nitrogen atom,
e) $R^2$ and $R^3$, together with the nitrogen to which they are bonded, form a 5- to 6-membered ring of the formula IV

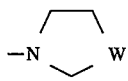 (IV)

in which W is
1) —CH$_2$—,
2) —CH$_2$—CH$_2$—,

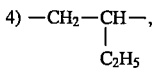

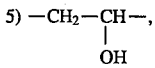

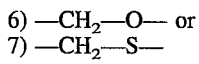

6) —CH$_2$—O— or
7) —CH$_2$—S—

R$^7$ is
  a) hydrogen
  b) alkyl having 1 to 17 carbon atoms,
  c) alkyl having 1 to 3 carbon atoms, mono- or polysubstituted by halogen,
  d) phenyl-(C$_1$–C$_2$)-alkyl; and
R$^8$ is
  a) hydrogen,
  b) methyl,
  c) alkenyl having 2 to 3 carbon atoms.

2. The method of claim 1, wherein said halogen is fluorine, chlorine, bromine, or iodine.

3. The method of claim 1, wherein said phenyl-(C$_1$–C$_2$)-alkyl is benzyl.

4. The method of claim 1, wherein
R$^1$ is
  a) hydrogen,
  b) alkyl having 1 to 6 carbon atoms,
  c) alkyl having 1 to 4 carbon atoms, mono- or polysubstituted by
     1) halogen,
  d) phenyl,
R$^2$ is
  a) hydrogen,
  b) alkyl having 1 to 4 carbon atoms,
  c) phenyl-(C$_1$–C$_2$)-alkyl,
  d) alkenyl having 2 to 3 carbon atoms,
R$^3$ is
  a) pyridyl, mono- or polysubstituted by
     1) hydrogen,
     2) halogen,
     3) nitro,
     4) alkyl having 1 to 3 carbon atoms,
     5) alkoxy having 1 to 3 carbon atoms,
  b) a radical of the formula II,

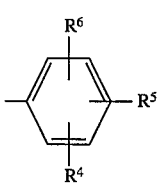 (II)

in which R$^4$, R$^5$, and R$^6$ can be identical or different and are
  1) hydrogen,
  2) alkyl having 1 to 3 carbon atoms, mono- or polysubstituted by 2.1 halogen,
3) R$^4$ is hydrogen and R$^5$ and R$^6$ form a methylene-dioxy radical,
4) alkoxy having 1 to 3 carbon atoms,
5) alkoxy having 1 to 3 carbon atoms, mono- or polysubstituted by
   5.1 halogen,
6) (C$_1$–C$_3$)-alkylmercapto,
7) (C$_1$–C$_3$)-alkylmercapto, mono- or polysubstituted by
   7.1 halogen,
8) nitro,
9) cyano,
10) (C$_1$–C$_3$)-alkylsulfonyl,
11) benzoyl,
12) benzoyl, mono- or polysubstituted by
    12.1 halogen,
    12.2 (C$_1$–C$_3$)-alkyl,
    12.3 (C$_1$–C$_3$)-alkoxy,
13) phenoxy,
14) phenoxy, mono- or polysubstituted by
    14.1 (C$_1$–C$_3$)-alkoxy, mono- or polysubstituted by 14.1.1 halogen,
    14.2 halogen,
    14.3 (C$_1$–C$_3$)-alkyl, mono- or polysubstituted by
         14.3.1 halogen,
c) a radical of formula III, —(CH$_2$)$_n$—COOR$^{10}$ (III)

in which R$^{10}$ is
  1) hydrogen,
  2) alkyl having 1 to 4 carbon atoms, n is an integer from 1 to 12,
d) R$^2$ and R$^3$, together with the nitrogen to which they are bonded, form a 4- to 9-membered ring, substituted by
  1) carbonyl on the carbon atom adjacent to the nitrogen atom,
R$^7$ is
  a) hydrogen,
  b) alkyl having 1 to 17 carbon atoms
  c) alkyl having 1 to 3 carbon atoms, mono- or polysubstituted by halogen,
  d) phenyl-(C$_1$–C$_2$)-alkyl, and
R$^8$ is
  a) hydrogen,
  b) methyl,
  c) alkenyl having 2 to 3 carbon atoms.

5. The method of claim 4, wherein said halogen is fluorine, chlorine, bromine, or iodine.

6. The method of claim 4, wherein said phenyl-(C$_1$–C$_2$)-alkyl is benzyl.

7. The method of claim 1, wherein
R$^1$ is alkyl having 1 to 6 carbon atoms,
R$^2$ is hydrogen,
R$^3$ is
  a) pyridyl, mono- or polysubstituted by halogen,
  b) a radical of the formula II,

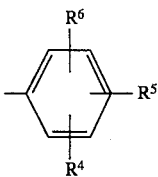

in which $R^4$, $R^5$, and $R^6$ can be identical or different and are
1) hydrogen,
2) alkyl having 1 to 3 carbon atoms, mono- or polysubstituted by
   2.1 halogen,
3) in which $R^4$ is hydrogen and $R^5$ and $R^6$ form a methylenedioxy radical,
4) alkoxy having 1 to 3 carbon atoms,
5) alkoxy having 1 to 3 carbon atoms, mono- or polysubstituted by
   5.1 halogen,
6) halogen,
7) nitro,
8) benzoyl,
9) benzoyl, mono- or polysubstituted by
   9.1 halogen,
   9.2 $(C_1-C_3)$-alkyl,
   9.3 $(C_1-C_3)$-alkoxy,
10) phenoxy,
11) phenoxy, mono- or polysubstituted by
   11.1 $(C_1-C_3)$-alkoxy, mono- or polysubstituted by 11.1.1 halogen,
   11.2 halogen,
   11.3 $(C_1-C_3)$-alkyl, mono- or polysubstituted by 11.3.1 halogen,
$R^7$ is alkyl having 1 to 17 carbon atoms, and
$R^8$ is hydrogen.

8. The method of claim 7, wherein said halogen is fluorine, chlorine, bromine, or iodine.

9. The method of claim 1, wherein said compound is methylisoxazole-4-carboxylic acid-(4-trifluoromethyl)anilide or N-(4-trifluoromethylphenyl)-2-cyano-3-hydroxycrotonamide.

10. A compound of the formula I

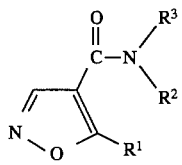

stereoisomeric forms thereof or physiologically tolerable salts thereof,
wherein
$R^1$ is
  a) hydrogen
  b) alkyl having 2 to 6 carbon atoms,
  c) alkyl having 1 to 4 carbon atoms, mono- or polysubstituted by
    1) halogen,
  d) phenyl,
$R^2$ is
  a) hydrogen,
  b) alkenyl having 2 to 3 carbon atoms,
  c) benzyl,
$R^3$ is
  a) pyridyl, mono- or polysubstituted by
    1) hydrogen,
    2) halogen,
    3) nitro,
    4) alkyl having 1 to 3 carbon atoms,
    5) alkoxy having 1 to 3 carbon atoms,
  b)

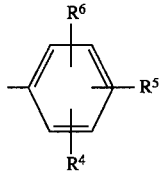

pyrimidinyl, mono- or polysubstituted by
    1) alkyl having 1 to 3 carbon atoms,
  c) indolyl or
  d) indazolinyl.

11. The compound of claim 10, wherein said halogen is fluorine, chlorine, bromine, or iodine.

12. A compound of claim 10, wherein
$R^1$ is
  a) hydrogen,
  b) alkyl having 2 to 6 carbon atoms,
  c) alkyl having 1 to 4 carbon atoms, mono- or polysubstituted by
    1) halogen,
  d) phenyl,
$R^2$ is
  a) hydrogen,
  b) alkenyl having 2 to 3 carbon atoms,
  c) benzyl,
$R^3$ is
  a) pyridyl, mono- or polysubstituted by
    1) hydrogen,
    2) halogen,
    3) nitro,
    4) alkyl having 1 to 3 carbon atoms,
    5) alkoxy having 1 to 3 carbon atoms,
  b)

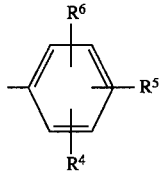

pyrimidinyl, mono- or polysubstituted by
    1) alkyl having 1 to 3 carbon atoms,
  c) indolyl, or
  d) indazolinyl.

13. The compound of claim 12, wherein said halogen is fluorine, chlorine, bromine, or iodine.

14. A compound of claim 10, wherein
$R^1$ is alkyl having 2 to 6 carbon atoms,
$R^2$ is hydrogen,
$R^3$ is pyridyl, mono- or polysubstituted by
    1) hydrogen,
    2) halogen.

15. The compound of claim 13, wherein said halogen is fluorine, chlorine, bromine, or iodine.

16. A compound of formula Ia or formula Ib

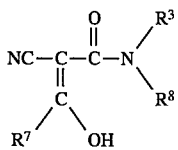

(Ia)

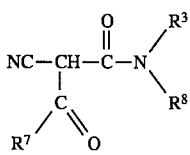

(Ib)

stereoisomeric forms thereof or physiologically tolerable salts thereof, where the radicals $R^7$, $R^8$, and $R^3$ are the following:

a) where $R^7$ is
1) hydrogen,
2) alkyl having 2 to 4 carbon atoms,
where $R^8$ is
1) hydrogen,
2) methyl,
where $R^3$ is
1) phenyl,
2) phenyl, mono- or polysubstituted by 2.1 halogen, 2.2 alkyl having 1 to 3 carbon atoms, mono- or polysubstituted by halogen, b) where $R^7$ is
1) alkyl having 1 to 4 carbon atoms,
2) hydrogen,
3) $CF_3$,
where $R^8$ is
1) hydrogen,
2) methyl,
3) alkenyl having 2 to 3 carbon atoms,
where $R^3$ is
1) pyridyl,
2) pyridyl, mono- or polysubstituted by 2.1 halogen, 2.2 alkyl having 1 to 3 carbon atoms,
3) pyrimidinyl, substituted as for 2),
4) thiazolyl, substituted as for 2), and 4.1 alkoxycarbonyl, having 1 to 3 carbon atoms in the alkyl chain,
5) benzothiazolyl, substituted as for 2),
6) benzimidazolyl, substituted as for 2),
7) indazolyl, substituted as for 2),
8) phenyl, mono- or polysubstituted by 8.1 benzoyl,
  8.2 benzoyl, mono- or polysubstituted by
    8.2.1 halogen,
    8.2.2 alkyl having 1 to 3 carbon atoms,
    8.2.3 alkoxy having 1 to 3 carbon atoms
    8.2.4 alkoxy having 1 to 3 carbon atoms, mono- or polysubstituted by halogen,
  8.3 carboxyl,
  8.4 hydroxyl, c) where $R^7$ is
1) hydrogen,
2) alkyl having 1 to 4 carbon atoms,
where $R^8$ is
1) hydrogen,
2) methyl,
where $R^3$ is
1) a radical of the formula III

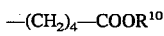 (III)

in which $R^{10}$ is
1.1 hydrogen
1.2 alkyl having 1 to 4 carbon atoms, d) wherein $R^7$ is
1) hydrogen,
2) alkyl having 1 to 4 carbon atoms,
$R^8$ and $R^3$ together with the nitrogen to which they are bonded, form a 4- to 9-membered ring, substituted by 2.1 carbonyl on the carbon atom adjacent to the nitrogen atom, or
$R^8$ and $R^3$, together with nitrogen to which they are bonded, form a piperidine ring optionally substituted by alkyl having 1 to 3 carbon atoms.

17. The compound of claim 16, wherein said halogen is fluorine, chlorine, bromine, or iodine.

18. A compound of claim 16, wherein the radicals $R^7$, $R^8$, and $R^3$ are the following a)
where $R^7$ is alkyl having 2 to 4 carbon atoms,
where $R^8$ is hydrogen,
where $R^3$ is
1) phenyl,
2) phenyl, mono- or polysubstituted by
  2.1 halogen,
  2.2 alkyl having 1 to 3 carbon atoms, mono- or polysubstituted by halogen, b)
where $R^7$ is alkyl having 1 to 4 carbon atoms,
where $R^8$ is hydrogen,
where $R^3$ is
1) pyridyl,
2) pyridyl, mono- or polysubstituted by
  2.1 halogen,
  2.2 alkyl having 1 to 3 carbon atoms,
3) phenyl, mono- or polysubstituted by
  3.1 benzoyl,
  3.2 benzoyl, mono- or polysubstituted by
    3.2.1 halogen,
    3.2.2 alkyl having 1 to 3 carbon atoms,
    3.2.3 alkoxy having 1 to 3 carbon atoms,
    3.2.4 alkoxy having 1 to 3 carbon atoms, mono- or polysubstituted by halogen.

19. The compound of claim 18, wherein said halogen is fluorine, chlorine, bromine, or iodine.

20. The compound N-(5-indolyl)-5-methylisoxazole-4-carboxamide, N-(6-indazolyl)-5-methyl-isoxazole-4-carboxamide, N-(5-indazolyl)-5-methylisoxazole-4-carboxamide, N-(4,6-dimethyl-2-pyridyl)-5-methylisoxazole-4-carboxamide, or N-(4,6-dimethyl-2-pyrimidinyl)-5-methylisoxazole-4-carboxamide.

21. A pharmaceutical composition comprising a compound in one of claims 10–20 and a physiologically acceptable excipient.

22. A method for the treatment of leukemia, sarcomas, carcinoma, lymphoma, or skin cancer comprising the step of administering a pharmaceutically effective amount of a composition in one of claims 10–20 to a patient in need of such treatment.

* * * * *

UNITED STATES PATENT AND TRADEMARK OFFICE
CERTIFICATE OF CORRECTION

PATENT NO. : 5,494,911   Page 1 of 2
DATED : February 27, 1996
INVENTOR(S) : Robert R. BARTLETT et al.

It is certified that error appears in the above-indentified patent and that said Letters Patent is hereby corrected as shown below:

Claim 10, Col. 30, lines 6-14 and

Claim 12, Col. 30, lines 43-50, delete

"  (II) "

Claim 15, Col. 30, line 65, "Claim 13" should read --Claim 14--.

UNITED STATES PATENT AND TRADEMARK OFFICE
CERTIFICATE OF CORRECTION

PATENT NO.  : 5,494,911
DATED       : February 27, 1996
INVENTOR(S) : Robert R. Bartlett et al.

It is certified that error appears in the above-indentified patent and that said Letters Patent is hereby corrected as shown below:

In the title, line 2, HYDROXYALKYLIDENECYANOACET-AMIDES"
should read --HYDROXYALKYLIDENECYANOACETAMIDES--.

Signed and Sealed this

Twenty-fourth Day of December, 1996

Attest:

BRUCE LEHMAN

*Attesting Officer*  *Commissioner of Patents and Trademarks*